United States Patent
Nishizawa et al.

(10) Patent No.: US 9,759,662 B2
(45) Date of Patent: Sep. 12, 2017

(54) EXAMINATION DEVICE AND EXAMINATION METHOD

(71) Applicant: HITACHI KOKUSAI ELECTRIC INC., Tokyo (JP)

(72) Inventors: Akihito Nishizawa, Tokyo (JP); Daisuke Yoshida, Tokyo (JP); Junji Shiokawa, Tokyo (JP)

(73) Assignee: HITACHI KOKUSAI ELECTRIC INC., Tokyo (JP)

(*) Notice: Subject to any disclaimer, the term of this patent is extended or adjusted under 35 U.S.C. 154(b) by 0 days.

(21) Appl. No.: 15/309,901

(22) PCT Filed: May 19, 2015

(86) PCT No.: PCT/JP2015/064250
§ 371 (c)(1),
(2) Date: Nov. 9, 2016

(87) PCT Pub. No.: WO2015/182429
PCT Pub. Date: Dec. 3, 2015

(65) Prior Publication Data
US 2017/0160201 A1 Jun. 8, 2017

(30) Foreign Application Priority Data
May 29, 2014 (JP) ................. 2014-111760

(51) Int. Cl.
*G01J 3/28* (2006.01)
*G01N 21/65* (2006.01)
*G01N 21/956* (2006.01)

(52) U.S. Cl.
CPC ....... *G01N 21/65* (2013.01); *G01N 21/95607* (2013.01); *G01N 2021/95615* (2013.01); *G01N 2201/06113* (2013.01)

(58) Field of Classification Search
CPC ........ G01J 3/28; G01J 3/02; G01J 3/42; G01J 3/52; G01J 3/46; G01J 3/12; G01N 21/25; G01N 21/27; G01N 21/57
See application file for complete search history.

(56) References Cited

U.S. PATENT DOCUMENTS

2011/0026035 A1* 2/2011 Muto ................. A61B 3/102
356/456

FOREIGN PATENT DOCUMENTS

JP 2010-151801 A 7/2010

* cited by examiner

*Primary Examiner* — Abdullahi Nur
(74) *Attorney, Agent, or Firm* — Volpe and Koenig, P.C.

(57) ABSTRACT

An examination device implements examination of matter to a large object without moving the device as a whole. The intensity of Raman scattering light obtained by laser irradiation of the object to be examined is detected to detect an attached state of an attached matter on the object to be examined. Based on a laser light irradiation position imaged and a visible image captured by a camera, the laser light irradiation position and a pixel of the camera are associated with each other, whereby irradiation area information is generated. Based on the attached state of the attached matter and the irradiation area information, an image of the attached matter present in an area imaged by the pixel of the camera is generated, and the visible image captured by the camera and the image of the attached matter are synthesized to generate a synthesized image.

14 Claims, 11 Drawing Sheets

FIG. 8
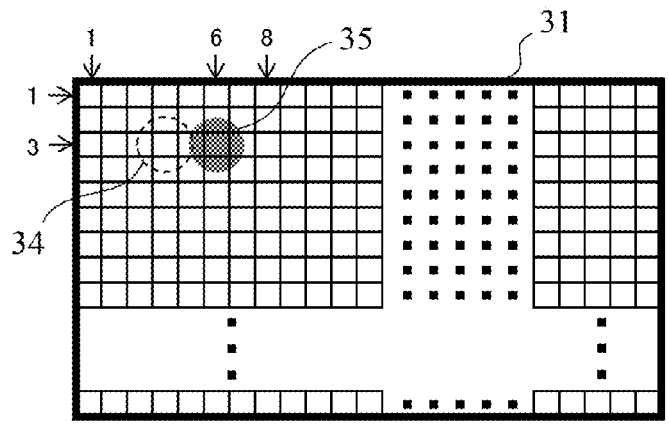
FIG. 9
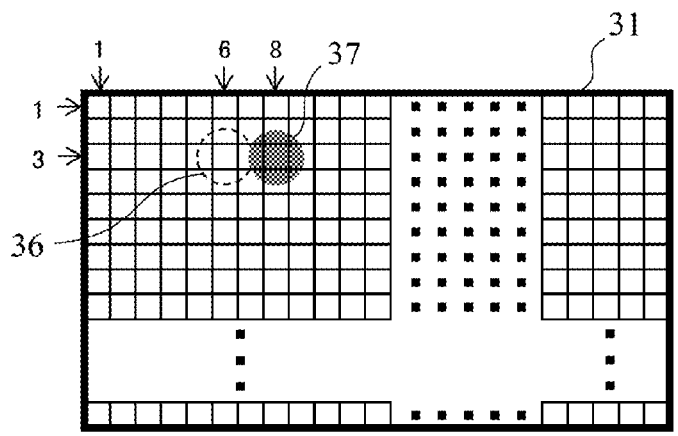
FIG. 10
| | T frame image | | | | | (T + 1) frame image | | | | |
|---|---|---|---|---|---|---|---|---|---|---|
| Horizontal pixel position | 5 | 6 | 7 | 8 | 9 | 5 | 6 | 7 | 8 | 9 |
| Vertical pixel position | 3 | 3 | 3 | 3 | 3 | 3 | 3 | 3 | 3 | 3 |
| Laser irradiation state | Part | Entire | Part | None | None | None | None | Part | Entire | Part |

EXAMINATION DEVICE AND EXAMINATION METHOD

TECHNICAL FIELD

The present invention relates to an examination device and examination method, and relates to a technology for identifying an attached matter on an object to be examined, for example.

BACKGROUND ART

In order to examine an attached matter attached to an object, the object may be irradiated with laser to obtain an image of the attached matter using scattered light (Raman scattering light) of the laser light. For example, in Patent Literature 1, Raman scattering light is caused to enter two-dimensionally arranged optical fibers, and light emitted from the other end of the optical fibers is dispersed into spectrum components of different wavelengths. The dispersed light of the wavelengths is received by a plurality of (two-dimensionally arranged) light receiving elements, and an image of the attached matter on the object to be examined is generated. Patent Literature 1 describes that, in this way, the attached matter can be rendered into an image so as to enable appropriate examination of the object to be examined.

CITATION LIST

Patent Literature

Patent Literature 1: JP 2010-151801 A

SUMMARY OF INVENTION

Technical Problem

However, according to Patent Literature 1, while examination can be performed in a two-dimensional region of the object to be examined, the configuration adopted is such that excitation laser light and Raman light are passed through one and the same macroscopic measurement objective lens (which is only capable of taking measurements in millimeters) for measurement. Accordingly, no consideration is given to handling large objects to be examined (for example, an object to be examined measuring 10 cm×10 cm). Because a microscope structure is adopted as the configuration of the examination device according to Patent Literature 1, the examination region is significantly limited, and the technology is unable to address the need for the ability to quickly examine larger objects to be examined.

The present invention has been made in view of the situation, and provides a technology for enabling implementation of an attached matter examination with respect to larger objects to be examined.

Solution to Problem

In order to solve the problem, according to the present invention, at least a part of an object to be examined is irradiated with light having a specific wavelength as a principal component, while an irradiation area is being modified. The irradiated position, on the object to be examined, of the light having the specific wavelength as a principal component, and a visible image of the object to be examined are captured by an imaging device. In addition, scattered light of the light irradiated onto the object to be examined is dispersed, and the intensity of the dispersed scattered light is detected. Based on the detected intensity of light, the attached state of an attached matter on the object to be examined is detected. From the irradiated position of the light having the specific wavelength as a principal component and the visible image that have been captured, the irradiated position of the light having the specific wavelength as a principal component and a pixel of the imaging device are associated with each other, whereby irradiation area information is generated. In addition, based on the attached state of the attached matter and the irradiation area information, an image of the attached matter present in an area captured by the pixel of the imaging device is generated. In addition, the visible image and the image of the attached matter are synthesized to generate a synthesized image.

Additional features associated with the present invention will become apparent from the following descriptions and the attached drawings. Various embodiments of the present invention may be achieved and implemented by elements and various combinations of elements, and by the embodiments described below and set forth in the appended claims.

It should be understood that the disclosure of the present description provides merely typical examples and is not intended to limit the scope of the claims or applications of the present invention in any sense.

Advantageous Effects of Invention

According to the present invention, attached matter examination can be implemented with respect to a large object to be examined.

BRIEF DESCRIPTION OF DRAWINGS

FIG. 8 is a diagram for describing an example of operation of an irradiation area detection unit 50.

FIG. 9 is a diagram for describing an example of operation of the irradiation area detection unit 50.

FIG. 10 is a diagram for describing an example of operation of the irradiation area detection unit 50.

DESCRIPTION OF EMBODIMENTS

In the following, embodiments of the present invention will be described with reference to the attached drawings. In the attached drawings, functionally identical elements may be denoted by the same numerals. While the attached drawings illustrate specific embodiments and implementation examples in accordance with the principle of the present invention, these are for facilitating an understanding of the present invention, and are not to be taken in interpreting the present invention in a limited sense.

The embodiments will be described to such sufficient extent as to enable one skilled in the art to carry out the present invention. However, other implementations or modes are also possible, and it should be understood that various modifications in configuration or structure and substitutions of various elements are possible without departing from the technical scope and spirit of the present invention. Accordingly, the following descriptions are not to be interpreted as limiting.

(1) First Embodiment

<Configuration of Examination Device>

Figure 1:
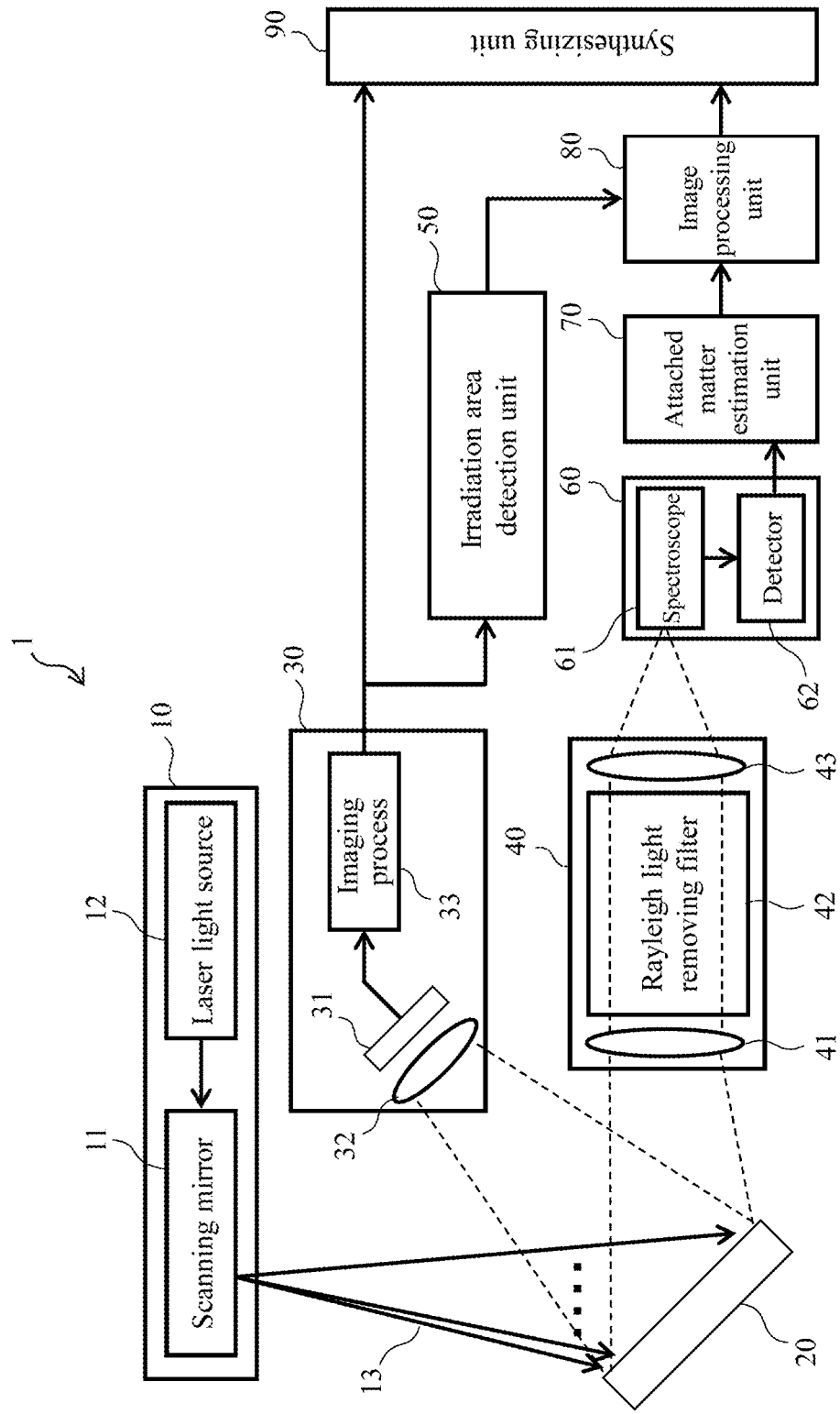
FIG. 1 is a diagram illustrating the configuration of an examination device according to the first embodiment of the present invention.

FIG. 1 is a diagram illustrating an overall configuration example of an examination device according to a first embodiment of the present invention. The examination device 1 includes a light irradiation unit 10 that irradiates an object 20 to be examined with light; a laser light path 13; a visible camera 30 that captures an image from the object 20 to be examined; a light condensing/filtering unit 40; a spectroscopic detection unit 60; an attached matter estimation unit 70; an image processing unit 80; an irradiation area detection unit 50; and a synthesizing unit 90. The light irradiation unit 10 includes a scanning mirror 11 and a laser light source 12. The visible camera 30 includes a camera lens 32; an imaging element 31; and an imaging process 33. The light condensing/filtering unit 40 includes lenses 41 and 43, and a Rayleigh light removing filter 42. The spectroscopic detection unit 60 includes a spectroscope 61 and a detector 62. In a stage preceding the spectroscope 60 (alternatively, in or in a stage preceding the light condensing/filtering unit 40), a filter for removing visible light (external light) may be provided.

In the examination device 1, the laser light output from the laser light source 12 is irradiated by the scanning mirror 11 onto the object 20 to be examined while the irradiated position is changed. Meanwhile, the object 20 to be examined is captured by the visible camera 30 including the camera lens 32, the imaging element 31, and the imaging process 33. In addition, the light condensing/filtering unit 40 condenses scattered light generated by the laser light irradiation of the object 20 to be examined, using the lens 41; removes Rayleigh scattered light using the Rayleigh light removing filter 42; and condenses and inputs the Raman scattering light into the spectroscope 61, using the lens 43. The spectroscopic detection unit 60 disperses the light input to the spectroscope 61 according to wavelength, using a diffraction grating or the like, and detects the dispersed light, using the detector 62. The attached matter estimation unit 70 generates a wavelength-by-wavelength light amount distribution from the result of detection by the detector 62, and detects a substance attached state, based on the state of the light amount distribution. The image processing unit 80 generates an image of the attached matter in accordance with the substance attached state (i.e., a grayscale image corresponding to the degree of scattering of the attached matter is generated). For example, in the case of a tire mark, carbon may be detected as the attached matter, or detection may be made focusing on differences in the amount of dust attached. The image processing unit 80 generates the image of the attached matter, using a signal from the visible camera 30 and based on position information generated by the irradiation area detection unit 50 indicating the position at which the object 20 to be examined has been irradiated with the laser to provide the relevant information. The synthesizing unit 90 is operated to synthesize an image of the attached matter with an image of the visible camera 30, and to cause a resultant image to be displayed on a display device, which is not illustrated. In the present embodiment, the light irradiation unit 10 employs laser light; however, LED light may be used as long as the principal component of the wavelengths corresponds to a specific wavelength.

<Example of Laser Irradiation>

Figure 2:
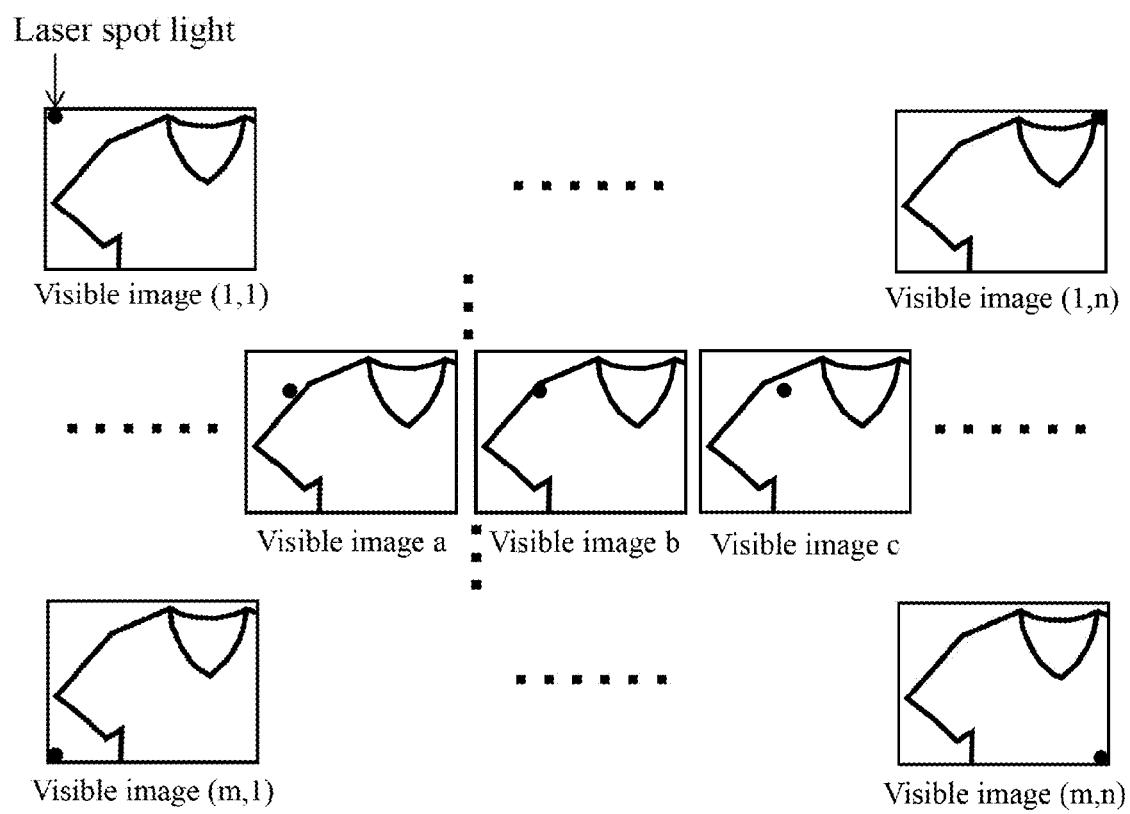
FIG. 2 is a diagram illustrating a relationship between laser scanning and a visible image.

FIG. 2 is a diagram illustrating an example of laser irradiation performed with respect to the object 20 to be examined, using the scanning mirror 11. A visible image (1, 1) illustrated in FIG. 2 represents an output image of the visible camera 30 at a certain arbitrary time t; a visible image (1, n) represents an output image, of the visible camera 30 of the (1×n)-th frame as counted from time t. As the number of frames increases, the scanning mirror 11 starts a scan of laser light from upper-left, and implements the scan toward lower-right. In this embodiment, the scan is implemented in all of photography regions photographed by the visible camera 30. However, if the portion to be examined is known in advance, the scan may be limited to the portion to be examined. With regard to the scan method, any overlap in the sequence or irradiated point need not be taken into consideration as long as the portion to be examined is irradiated with laser, because the laser irradiation position is identified from the image of the visible camera 30. By thus generating an image by Raman scattering light while confirming the laser spot position using a visible image, the position of the attached matter image in the visible image is clarified. Accordingly, no positional calibration at the time of laser irradiation is required. There is also no need to adopt a microscope structure, so that a large object to be examined can be measured. In addition, by increasing or decreasing the diameter of laser irradiation in accordance with the object to be examined, the photographed images, i.e., the number of frames, can be optimized, enabling a decrease in measurement time. While in the present embodiment, a visible camera is used, the camera may not be limited to the visible light wavelength region as long as the camera is capable of photographing the laser light used.

<Output of Raman Scattering Light>

Figure 3:
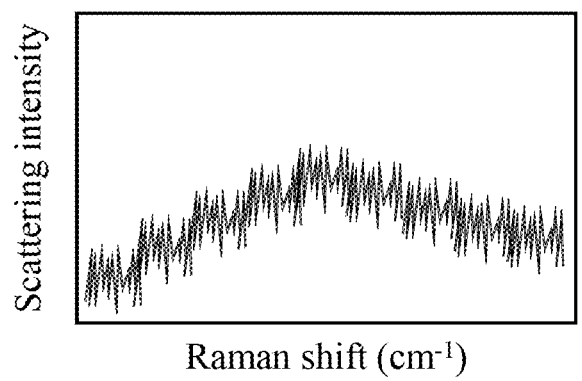
FIG. 3 is a diagram illustrating an example of an output signal from a detector 62 where there is no attached matter.
Figure 4:
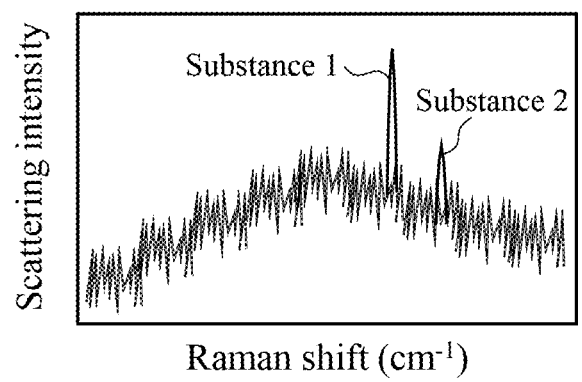
FIG. 4 is a diagram illustrating an example of an output signal from the detector 62 where there is an attached matter.
Figure 5:
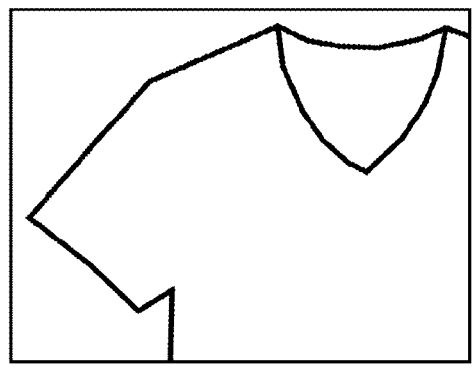
FIG. 5 is a diagram illustrating an example of an output signal from an imaging process 33.
Figure 6:
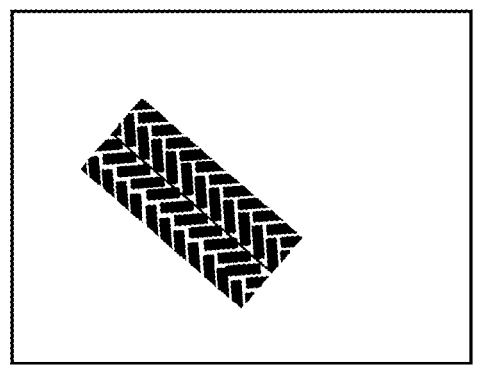
FIG. 6 is a diagram illustrating an example of an output signal from an image processing unit 80.

FIGS. 3 and 4 are diagrams illustrating examples of the output of the spectroscopic detection unit 60. FIG. 5 illustrates an output image of the visible camera 30. FIG. 6 illustrates an output image of the image processing unit 80.

Figure 7:
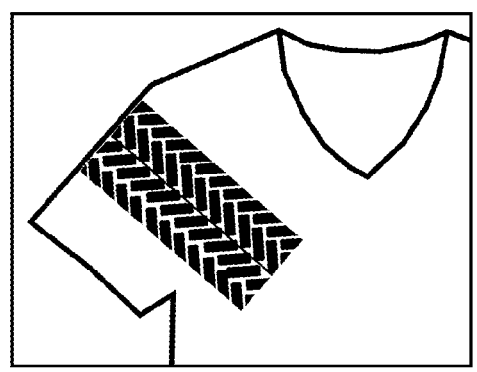
FIG. 7 is a diagram illustrating an example of an output signal from a synthesizing unit 90.

FIG. 7 is a diagram illustrating an example of an image generated by the synthesizing unit 90.

The output examples illustrated in FIGS. 3 and 4 are those of signals obtained by removing unwanted light from the light emitted or reflected from the object 20 to be examined, using the condensing/filtering unit 40, condensing only the Raman scattering light generated by the laser irradiation (for example, the Raman scattering light that has a higher frequency than the frequency component of the laser light), and then processing the condensed Raman scattering light using the spectroscopic detection unit 60. The Raman scattering light is light of a wavelength that has been shifted, by a certain amount, from the wavelength of the irradiated laser light, which is irradiated in accordance with the molecular oscillation energy amount of substance. Accordingly, when examination is performed at two locations to which different attached matters have become attached, different outputs as illustrated in FIG. 3 and FIG. 4 can be obtained as the output of the spectroscopic detection unit 60 (detector 62).

For example, if a vehicle has been moved (run) over a shirt, the substance that becomes attached differs between the groove and tread portions of the tire. Thus, by handling the shirt as the object to be examined, and by examining Raman scattering light from the shirt, an image of tire mark as illustrated in FIG. 6 can be obtained. The substance may be a specific substance, or a mixture of a plurality of substances. The tire mark is detected by detecting the laser spot position from the output image of FIG. 5 from the visible camera 30, using the irradiation area detection unit 50. Accordingly, the outputs from the visible camera 30 and the image processing unit 80 can be easily synthesized using the position information from the irradiation area detection unit 50, despite the fact that the respective optical systems are different. In addition, positional calibration at the time of laser spot position irradiation can be omitted, whereby an easy-to-use device that does not require a touch to a laser light portion thereof and is therefore safe can be provided.

<Irradiation Area Detection Process>

FIGS. 8, 9, and 10 are diagrams for describing the operation of the irradiation area detection unit 50. In FIGS. 8 and 9, the lattice-shaped thin frames represent the light receiving elements in the imaging element 31, and are horizontally and vertically numbered to indicate the position of the light receiving elements. A laser light spot 35 and a laser light spot 37 illustrate the reception of the laser light spot on an imaging surface. A laser light spot 34 and a laser light spot 36, which are indicated by broken lines, represent the laser light spot positions in the previous field.

In FIG. 8, the laser light spot 35 is impinging on the entire light receiving element at the position of horizontal 6 and vertical 3, with the laser light spot 35 partially impinging on the pixels peripheral to the light receiving element at the position of horizontal 6 and vertical 3. Similarly, in FIG. 9, the laser light spot 37 is impinging on the entire light receiving element at the position of horizontal 8 and vertical 3, with the laser light spot 37 partially impinging on pixels peripheral to the light receiving element at the position of horizontal 8 and vertical 3. FIG. 9 illustrates the field following the field of FIG. 8. Accordingly, when FIG. 8 is the T-th frame, FIG. 9 is the (T+1)-th frame.

FIG. 10 illustrates the relationship between the laser light spots in the T and (T+1)-th frames and the horizontal and vertical pixel positions. In FIG. 10, at the position of horizontal 6 and vertical 3 and the position of horizontal 8 and vertical 3, the T-th frame and the (T+1)-th frame respectively are being irradiated with laser light. Accordingly, Raman scattering light acquisition is performed in the frames being irradiated with laser light, and attached substance detection is performed. In addition, at the position of horizontal 7 and vertical 3, the light receiving element is partially being irradiated with laser light in both of the T-th frame and the (T+1)-th frame. Accordingly, attached substance detection is performed from the result of Raman scattering light acquisition in the two fields. In this way, the position of the light receiving element and the acquisition of Raman scattering light are associated with each other, and attached substance detection is performed from the state of Raman scattering light at each position, whereby the attached matter can be rendered into an image as illustrated in FIG. 6, in accordance with the degree of attachment. The image of the attached matter is created simultaneously with the imaging of a visible image while confirming the image using the visible camera 30, and the rendering into an image or image data is performed at the position corresponding to the sampling position for the object to be examined at the time of generating the image by the visible camera 30. In this way, the image generated by the visible camera 30 and the image or image data of the attached matter generated by the image processing unit 80 are generated with respect to the same position of the object to be examined. Accordingly, the images can be synthesized without having to consider differences therebetween, despite the fact that the respective optical systems are different.

According to the present embodiment, the object to be examined is irradiated with laser light directly, and the laser light is scanned on the object to be examined while the laser light irradiation position is confirmed by acquiring a visible image, whereby the effect of enabling the examination of a large object to be examined can be expected. In addition, an image or image data of the attached matter is generated so as to correspond to the position of sampling, by the visible light camera 30, of the object to be examined at the time of photographing the object to be examined by the visible light camera 30. Accordingly, the image photographed by the visible light camera 30 and the image of the attached matter can be simply synthesized without becoming aware of the difference in optical systems. In addition, there is no need to perform calibration of the laser irradiation position. Further, the number of frames used for examination can be optimized by varying the laser spot diameter, so that, particularly when the spot diameter is increased, the measurement time can be decreased. However, it may become necessary to decrease the laser light scanning speed compared to the imaging speed for the visible image. This is because if the scan speed is made faster than the imaging speed, correspondence between the visible image and the Raman scattering light may fail to be achieved.

In the embodiment of the present invention, basically, a scan is performed on a light receiving element by light receiving element (dot by dot) basis; as a development for achieving higher throughput, a scan is performed at intervals (for example, every other light receiving element is scanned); and, with regard to the light receiving element that is only partly irradiated with laser light, an image of the skipped light receiving element is interpolated using the Raman scattering light of a plurality of fields.

(2) Second Embodiment

<Configuration of Examination Device>

Figure 11:
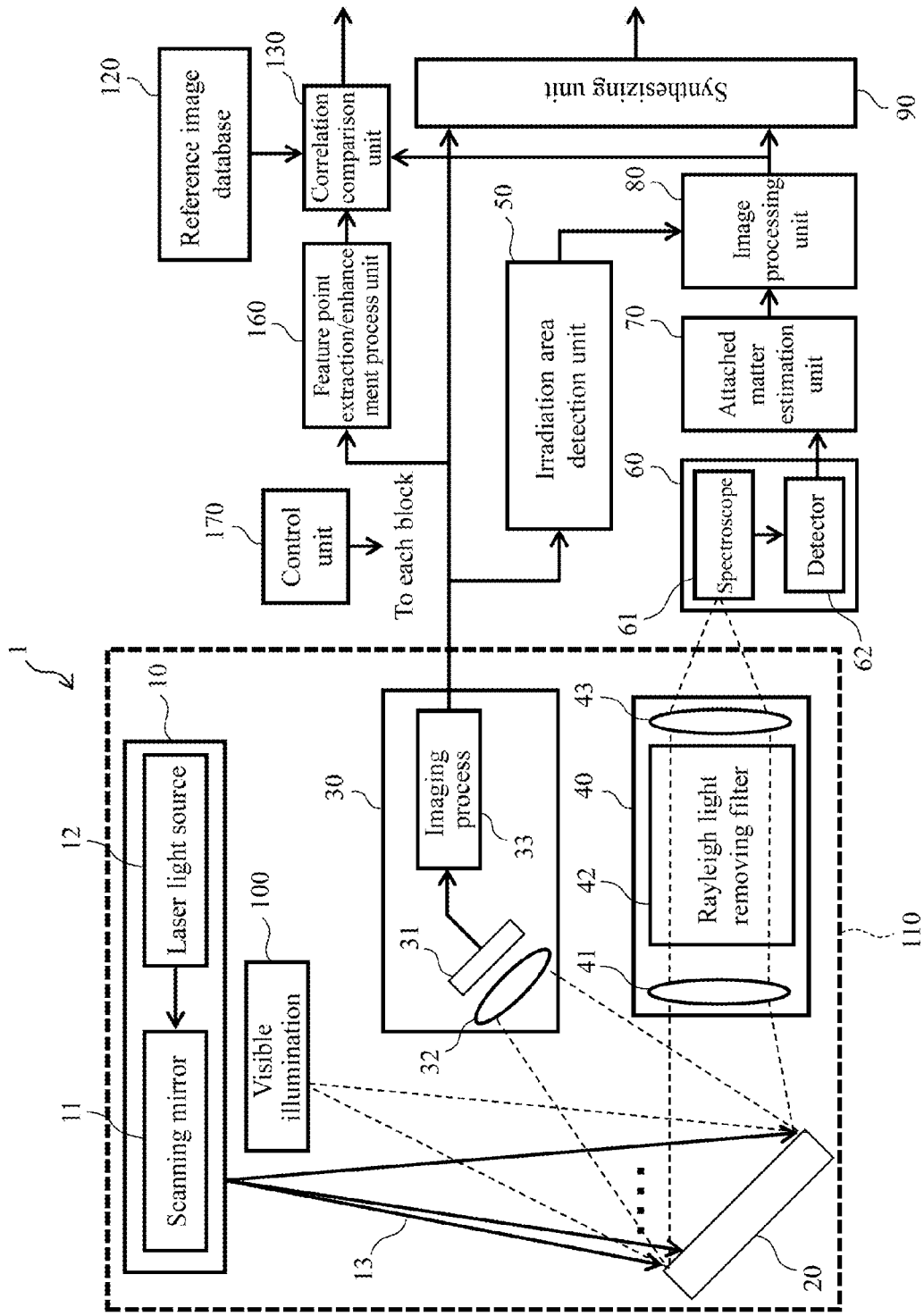
FIG. 11 is a diagram illustrating the configuration of an examination device according to the second embodiment of the present invention.

FIG. 11 is a diagram illustrating the overall configuration of the examination device 1 according to a second embodiment of the present invention. In FIG. 11, portions overlapping with those of FIG. 1 are designated with identical numerals, and their descriptions are omitted. The examination device 1 according to the second embodiment includes, in addition to the configuration of the examination device 1 according to the first embodiment (FIG. 1), a visible light illumination 100 as a means for irradiating second light; a control unit 170; a feature point extraction/enhancement process unit 160; a reference image database 120; a correlation comparison unit 130; and a light-shield housing (light-shield region) 110. In the examination device 1 according to the second embodiment, the object 20 to be examined, the light irradiation unit 10, the visible light illumination 100, the visible camera 30, and the light condensing/filtering unit 40 are separated from the other portions by the light-shield housing 110 so as to eliminate the influence of external light.

In the examination device 1 according to the second embodiment, the feature point extraction/enhancement process unit 160 executes a visibility increasing process for enhancing the image contrast and the like with respect to the image of the visible camera 30. The correlation comparison unit 130 compares the image subjected to the visibility increasing process and the image or image information of the attached matter created by the image processing unit 80, with reference images stored in the reference image database 120, so as to identify the image type.

The control unit 170 performs control of the light amount of the laser light from the light irradiation unit 10, the turning-on and off of the laser light source, and the light amount or turning-on and off of the visible light illumination 100, for example. When the object to be examined is a tire mark or the like attached to clothing, it is often the case that a glimpse of tire mark is present that may be faintly visible. In such case, an image that has been subjected to an enhancement process for increasing the visibility of a wide area including the glimpse, and the image of the attached matter created by the image processing unit 80 are combined, and the combined image is compared with tire tread patterns in the reference image database 120. In this way, the tire brand can be quickly and accurately identified. In addition, if the examination object can be narrowed down to a partial area of the examination object based on the glimpse, the control unit 170 narrows down the area of light irradiation by the light irradiation unit 10. In this way, the speed of examination can be increased. With regard to the glimpse, feature points may be extracted from the image of the visible camera 30 so as to narrow down a candidate region, or an area may be set by visual examination. In the present embodiment, the light irradiation unit 10, the visible light illumination 100 as a means for irradiating the second light, and the visible camera 30 are being described within the visible light wavelength range. However, the visible light is not a limitation and, instead of the visible camera 30, any other cameras having sensitivity in the wavelength used may be used. For example, ultraviolet or near-infrared light may be used, and still a comparable effect can be obtained <Details of Operation of Examination Device>

Figure 12:
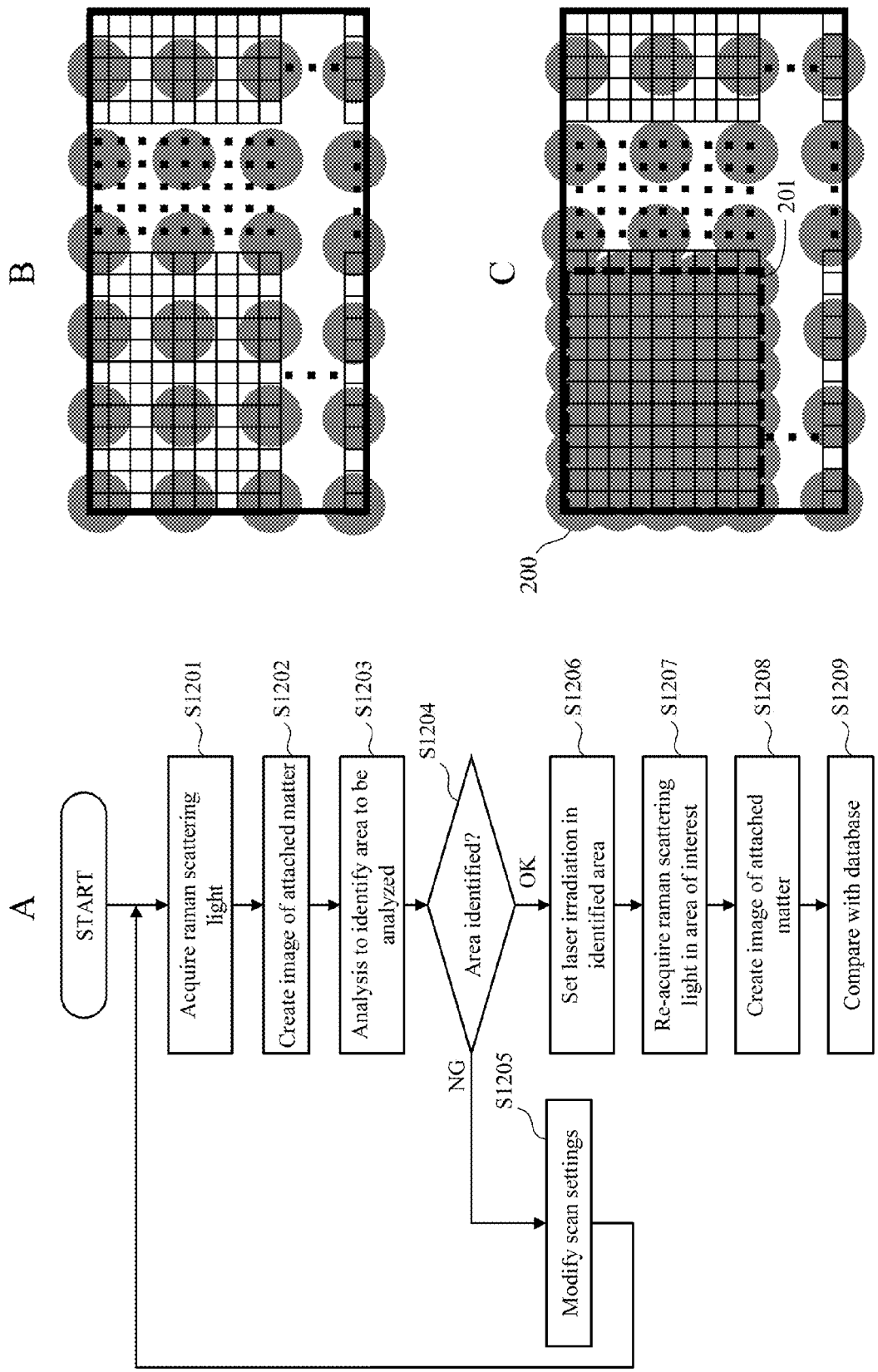
FIG. 12A is a flowchart for describing the operation of a control sequence.
FIG. 12B is a diagram for describing the operation for identifying an analysis area by acquiring Raman scattering light discretely.
FIG. 12C is a diagram for describing the operation for generating an attached matter image by acquiring Raman scattering light continuously in the identified analysis area.

FIGS. 12A to 12C are diagrams for describing the details of operation of the examination device 1 according to the second embodiment. FIG. 12A is a flowchart for describing the operation of the examination device 1. FIG. 12B is a diagram indicating the position of the light irradiation from the light irradiation unit 10 when the examination area is narrowed down in the object to be examined. FIG. 12C is a diagram indicating the position, added to FIG. 12B, of the light irradiation from the light irradiation unit 10 at the time of a detailed examination after the examination area has been narrowed down. In FIGS. 12B and 12C, the gray circular patterns indicate the laser light irradiation positions, representing, on the imaging surface, all of the positions irradiated with laser light at the time of examination. The small lattice-shaped frames represent the light receiving elements in the imaging element 31, as in FIG. 8.

S1201: The control unit (processor) 170, starting from the point in time of completion of examination preparation, causes the examination device 1 to operate to take the laser irradiation position discretely, and acquire Raman scattering light discretely, as illustrated in FIG. 12B.

S1202: The control unit 170 generates an image from the Raman scattering light. If the laser irradiation position corresponds to the position of the attached matter, an image of the attached matter is generated; if not, an image of the attached matter cannot be acquired.

S1203: The control unit 170 examines an area of attachment (area to be analyzed) of the attached matter, from the image of the Raman scattering light.

S1204: The control unit 170 determines the appropriateness of the area to be analyzed identified in S1203. If the area of attachment of the attached matter can be identified (OK in S1204), the process transitions to S1206. If the area of attachment of the attached matter cannot be identified (NG in S1204), the process transitions to S1205.

S1205: The control unit 170 modifies the laser light scan settings used in S1201. For example, the interval of discrete irradiation is narrowed, the laser intensity is increased, or the scan location is modified. After the settings are modified, the process again transitions to S1201.

S1206: The control unit 170, in order to scan the identified range in greater detail, sets various laser conditions.

S1207: The control unit 170, with respect to a location of acquisition failure (portion skipped by discrete scan) in the identified range (area to be analyzed), causes the examination device 1 to operate to acquire Raman scattering light again.

S1208: The control unit 170 causes the examination device 1 to operate to create an image of the attached matter based on the Raman scattering light acquired in S1206.

S1209: The control unit 170 compares the image acquired in S1207 with the images registered in the reference image database 120.

If a region 201 illustrated in FIG. 12C is the area to be analyzed, the control unit 170 causes the examination device 1 to operate to perform laser irradiation again with respect to non-gray, white portions in the area to be analyzed in FIG. 12B, so as to eliminate non-measured portions in the region 201, as illustrated in FIG. 12C. In this way, the locations for measuring Raman scattering light are decreased, thereby achieving high speed.

<Visible Light Irradiation and Laser Irradiation Timing>

Figure 13:
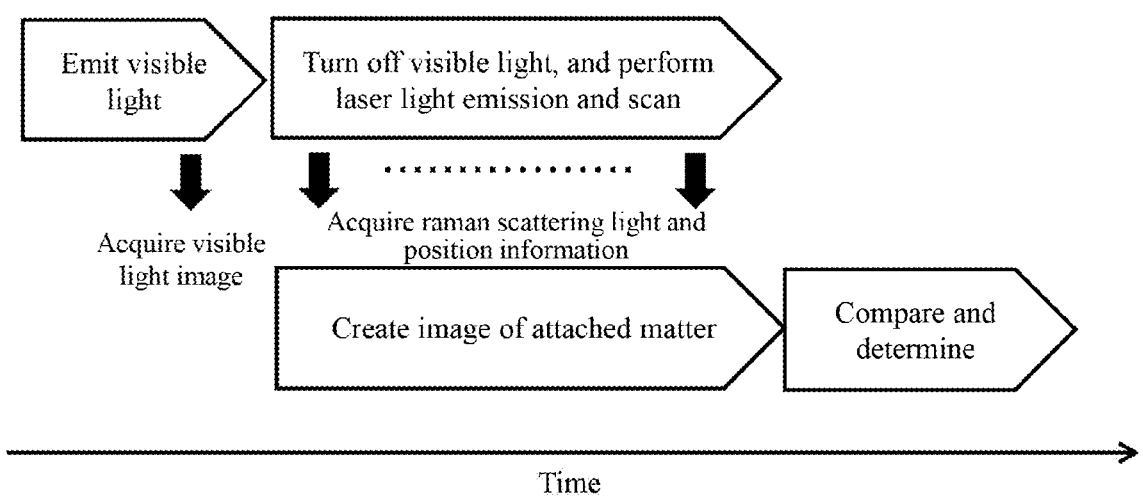
FIG. 13 is a diagram illustrating an operating example of visible illumination and laser light irradiation timing.

FIG. 13 is a diagram illustrating the timing of turning on and off the light irradiation unit 10 and the visible light illumination 100 in the second embodiment. In the second embodiment, initially only the visible light illumination 100 is turned on, and a visible image is acquired from the visible camera 30. Then, the visible light illumination 100 is turned off, the light irradiation unit 10 irradiates laser, Raman scattering light is acquired while varying the laser irradiated position, and an image or image data of the attached matter is created. In this way, it becomes possible to increase measurement accuracy by reducing the external light that becomes included during Raman scattering light acquisition. According to the present embodiment, as in the first embodiment (FIG. 1), an image or image data of the attached matter is created in correspondence to the pixel position of the imaging element 31, so that effects similar to those according to the first embodiment can be expected. In addition, in the present embodiment, the portion requiring examination in the area of the object to be examined is initially determined, and then examination is performed with respect to the determined portion, whereby the examination speed can be increased. In addition, in the present embodiment, the circular area shown in gray is slightly larger compared to the cases described with reference to FIGS. 8 and 9. This means that, while the image or image data of the attached matter is likewise created at the position of the light receiving element in the imaging element 31, high speed is achieved by slightly reducing the resolution of the image or the image per se of the image data. By thus optimizing the laser spot diameter according to the purpose, in addition to the limitation of the examined location, high examination speed can be achieved.

(3) Third Embodiment

<Configuration of Examination Device>

Figure 14:
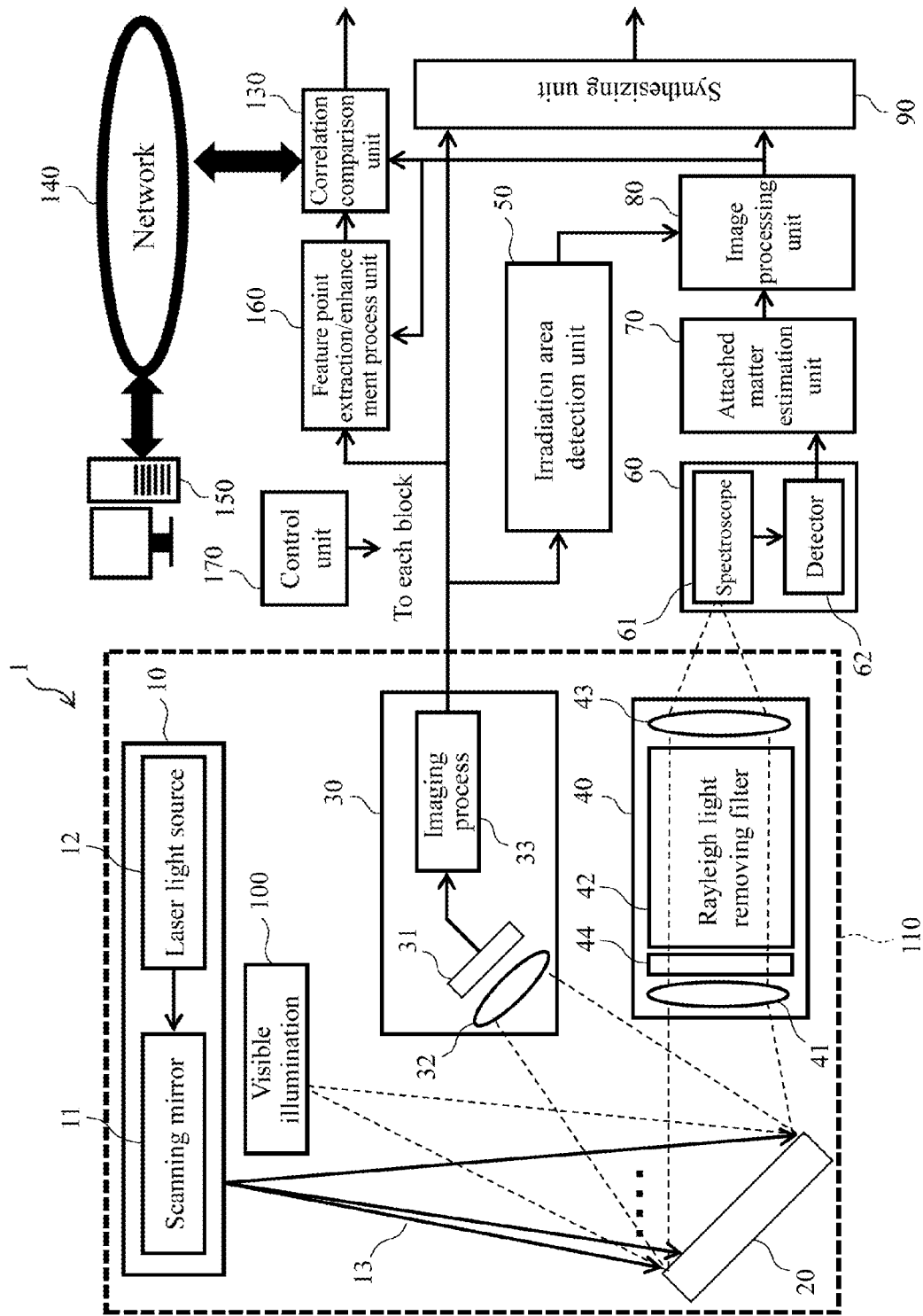
FIG. 14 is a diagram illustrating the configuration of an examination device according to the third embodiment of the present invention.

FIG. 14 is a diagram illustrating the overall configuration of the examination device 1 according to a third embodiment of the present invention. In FIG. 14, portions overlapping with those of FIGS. 1 and 11 are designated with identical numerals and their description is omitted.

The examination device 1 according to the third embodiment, compared with the second embodiment (FIG. 11), adopts the configuration additionally provided with a data center 150 and a network 140, wherein the reference image database 120 is stored in the data center connected to the network. In addition, in the examination device 1, the wavelengths used for the light of the light irradiation unit 10 and the visible light illumination 100 are separated, thereby eliminating the turn-on/off control of the light irradiation unit 10 and the visible light illumination 100.

<Operation of Examination Device>

Figure 15:
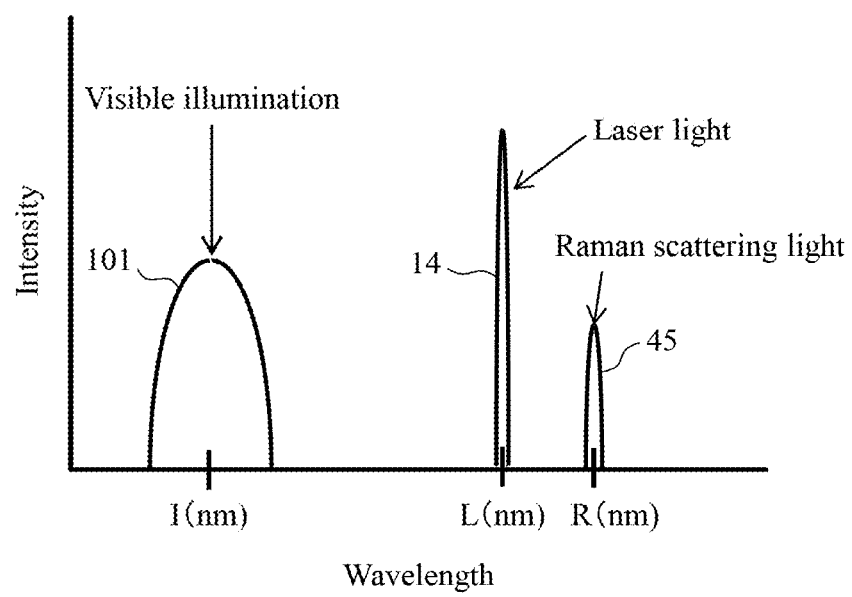
FIG. 15 is a diagram illustrating a distribution state of light before passing a light condensing/filtering unit.
Figure 16:
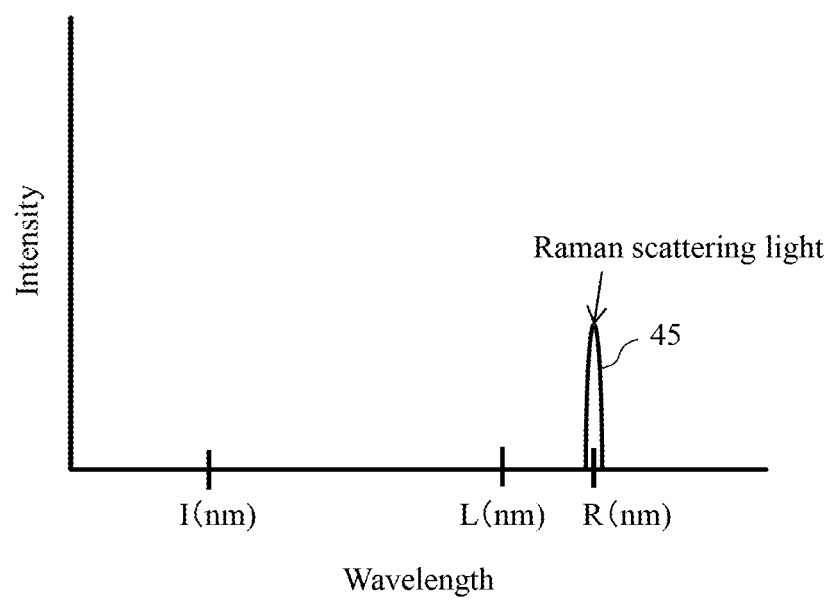
FIG. 16 is a diagram illustrating a distribution state of light after passing the light condensing/filtering unit.

FIGS. 15 and 16 are diagrams for describing the operation of the examination device 1 according to the present embodiment.

FIG. 15 illustrates an example of wavelengths used in the light irradiation unit 10 and the visible light illumination 100, where the wavelength of the laser light of the light irradiation unit 10, and the wavelength of the visible light illumination 100 are made separable by the optical filter 44. The optical filter 44 is disposed in the light condensing/filtering unit 40 illustrated in FIG. 14. In the third embodiment, when laser light is irradiated, as illustrated in FIG. 15, three types of light, namely, laser light, visible light illumination, and Raman scattering light, enter the light condensing/filtering unit 40. The incident light passes through the light condensing/filtering unit 40, whereby only the Raman scattering light remains, as illustrated in FIG. 16 (only the Raman scattering light on the higher frequency side than the laser light). From the Raman scattering light, an image or image data of the attached matter is created.

In the third embodiment, the database storage location of the reference image is changed, and the light turn-off/turn-on control is eliminated by separating the emitted light by wavelength, whereby substantially equal and comparable effects to those of the first and second embodiments (FIG. 1 and FIG. 11) can be obtained. In addition, by eliminating the turn-off/turn-on control, the effect of simplified system control can be achieved.

(4) Fourth Embodiment

Figure 17:
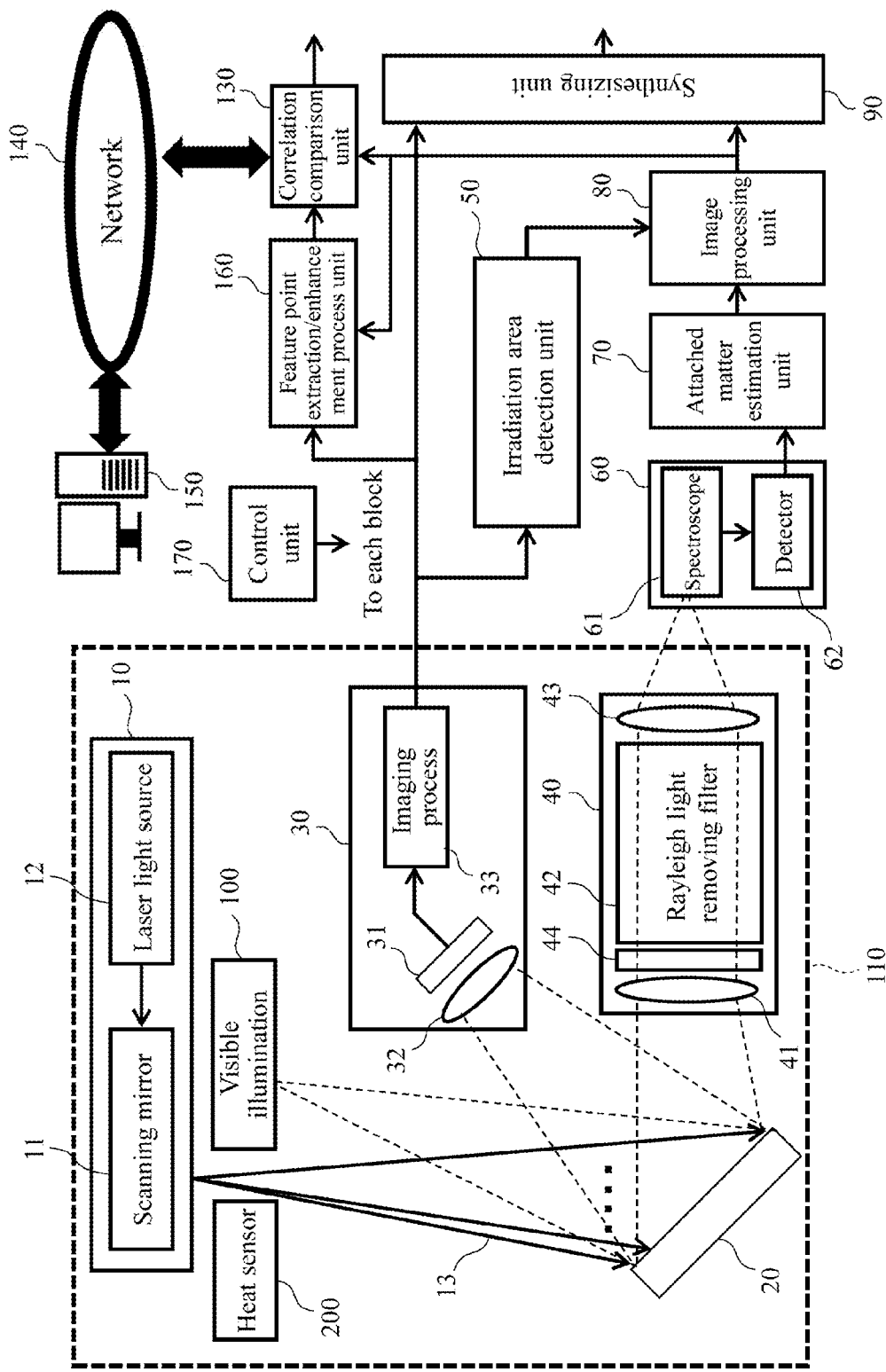
FIG. 17 is a diagram illustrating the configuration of an examination device according to the fourth embodiment of the present invention.

FIG. 17 is a diagram illustrating the configuration of the examination device 1 including a heat sensor 200 in addition to the configuration of the third embodiment.

While laser light is irradiated to measure Raman scattering light, if the light amount of the laser light is excessive, there is the possibility of damaging or burning the object to be examined. In order to solve the problem, in the examination device 1 according to the fourth embodiment, the temperature of the laser spot position is monitored by means of the heat sensor 200. In the examination device 1, when the temperature of the laser spot position being monitored reaches a designated value or above, the control unit 170 operates to limit the laser output of the light irradiation unit 10 so as to protect the object to be examined. The examination device according to the fourth embodiment can provide essentially equal and comparable effects to those of the examination devices according to the first to third embodiments (FIGS. 1 and 11 and FIG. 14).

(5) Others

While in the third and fourth embodiments, the reference image database 120 is stored in the data center 150 connected to the examination device 1 via the network 140, the reference image database 120 may be connected to the examination device 1 without an intervening network, as in the second embodiment. Accordingly, it should be noted that the filter 44 is provided not because of the connection to the reference image database via the network 140.

In the examination device 1 according to the second to fourth embodiments, the light-shield housing 110 accommodates the light irradiation unit 10, the visible light illumination 100, the object 20 to be examined, the visible camera 30, and the light condensing/filtering unit 40. However, the light-shield housing is not a requirement, and any light shield means capable of preventing exposure of the various units to external light may be adopted.

As described above, according to the present invention, the object to be examined is scanned with the laser spot light, while at least a part of the object to be examined is imaged by an imaging device (camera), the image by the camera and the acquisition of Raman scattering light are synchronized, and the position at which the Raman scattering light has been acquired is identified from the position of the laser spot imaged by the camera. In this way, examination of a large attached matter (such as a tire mark attached to clothing due to traffic accident, for example) can be implemented without being limited by the size of the object to be examined.

The present invention is not limited to the configurations of the above-described first to fourth embodiments, and may include various modifications. The embodiments have been described for facilitating an understanding of the present invention, and are not limited to include all of the described configurations. A part of the configuration of one embodiment may be substituted by the configuration of another embodiment, or the configuration of the other embodiment may be incorporated into the configuration of the one embodiment. In addition, with regard to a part of the configuration of each embodiment, addition, deletion, or substitution of other configurations may be made. For example, the reference image database 120, the feature point extraction/enhancement process unit 160, and the correlation comparison unit 130 included in the examination device 1 according to the second embodiment may be introduced into the examination device 1 according to the first embodiment. In addition, the above-described configurations may be partly or entirely configured from hardware, or configured to be implemented when a program is executed by a processor. The control lines and information lines illustrated are only those contemplated to be necessary for the purpose of description, and do not necessarily represent all of the control lines or information lines of a product. It may be contemplated that in practice, almost all of the configurations are mutually connected.

REFERENCE SIGNS LIST

1 Inspection device
10 Light irradiation unit
11 Scanning mirror
12 Laser light source
13 Laser light path
20 Object to be examined
31 Imaging element
32 Camera lens
33 Imaging process
30 Visible camera
40 Light condensing/filtering unit
41 Lens
42 Rayleigh light removing filter
43 Lens
44 Optical filter
50 Irradiation area detection unit
60 Spectroscopic detection unit
61 Spectroscope
62 Detector
70 Attached matter estimation unit
80 Image processing unit
90 Synthesizing unit
100 Visible light illumination
110 Light-shield housing
120 Reference image database
130 Correlation comparison unit
140 Network
150 Data center
160 Feature point extraction/enhancement process unit
170 Control unit
200 Heat sensor

The invention claimed is:

1. An examination device comprising:
a light irradiation unit that irradiates at least a part of an object to be examined with light having a specific wavelength as a principal component, while an irradiation area is being modified;
an imaging unit that images an irradiated position, on the object to be examined, of the light having the specific wavelength as a principal component, and that captures an image of the object to be examined;
a spectroscope that disperses scattered light of the light irradiated by the light irradiation unit onto the object to be examined;
a detector that detects an intensity of the scattered light dispersed by the spectroscope;
an attached state estimation unit that detects an attached state of an attached matter on the object to be examined from the intensity of the light detected by the detector;
an irradiation area detection unit that, from the irradiated position; captured by the imaging unit; of the light having the specific wavelength as a principal component and the captured image, generates irradiation area information by associating the irradiated position of the light having the specific wavelength as a principal component and a pixel of the imaging unit;
an image processing unit that, based on the attached state of the attached matter and the irradiation area information, generates an image of the attached matter present in an area imaged by the pixel of the imaging unit; and
a synthesizing unit that generates a synthesized image by synthesizing the captured image and the image of the attached matter.

2. The examination device according to claim 1, further comprising:
a visible light irradiation unit that irradiates the object to be examined with visible light;
a control unit that controls an irradiation timing of the visible light and the light having the specific wavelength as a principal component; and
a light shield that shields the light irradiation unit, the visible light irradiation unit, the imaging unit, and the object to be examined from external light.

3. The examination device according to claim 2, wherein the control unit switches the irradiation of the visible light and the irradiation of the light having the specific wavelength as a principal component.

4. The examination device according to claim 1, further comprising:
a visible light irradiation unit that irradiates the object to be examined with visible light;
a visible light removing filter removing visible light from the scattered light; and
a light shield that shields the light irradiation unit, the visible light irradiation unit, the imaging unit, the object to be examined, and the visible light removing filter from external light.

5. The examination device according to claim 1, further comprising:
a comparison unit that compares the image of the attached matter with a plurality of reference attached matter images stored in a reference image database.

6. The examination device according to claim 5, further comprising a control unit that controls the irradiation area by the light irradiation unit,
wherein the control unit controls the light irradiation unit to discretely irradiate the object to be examined with the light having the specific wavelength as a principal component, causes the image processing unit to generate a first attached matter image, identifies an area to be analyzed based on the first attached matter image, controls the light irradiation unit to irradiate the area to be analyzed with light, causes the image processing unit to generate a second attached matter image, and causes the comparison unit to compare the second attached matter image with the plurality of reference attached matter images.

7. The examination device according to claim 1, further comprising:
a temperature sensor that measures a temperature of the object to be examined during irradiation of the light having the specific wavelength as a principal component; and
a control unit that, based on the temperature measured by the temperature sensor, controls the irradiation by the light irradiation unit of the light having the specific wavelength as a principal component.

8. An examination method for examining an attached matter on an object to be examined, the method comprising:
irradiating at least a part of the object to be examined with light having a specific wavelength as a principal component, while modifying an irradiation area;
imaging an irradiated position, on the object to be examined, of the light having the specific wavelength as a principal component, and capturing an image of the object to be examined, using an imaging device;

dispersing scattered light of the light irradiated onto the object to be examined;

detecting an intensity of the scattered light that has been dispersed;

detecting, from the detected intensity of the light, an attached state of the attached matter on the object to be examined;

generating, from the imaged irradiated position of the light having the specific wavelength as a principal component and the captured image, irradiation area information by associating the irradiated position of the light having the specific wavelength as a principal component with a pixel of the imaging device;

generating an image of the attached matter present in an area imaged by the pixel of the imaging device, based on the attached state of the attached matter and the irradiation area information; and generating a synthesized image by synthesizing the captured image and the image of the attached matter.

9. The examination method according to claim 8, further comprising:

irradiating the object to be examined with visible light; and controlling an irradiation timing of the visible light and the light having the specific wavelength as a principal component, wherein irradiating the light, irradiating the visible light, and capturing an image using the imaging device are executed while being shielded from external light.

10. The examination method according to claim 9, wherein controlling the visible light and the light having the specific wavelength as a principal component are irradiated while being switched.

11. The examination method according to claim 8, further comprising:

irradiating the object to be examined with visible light; and removing the visible light from the scattered light using a visible light removing filter, wherein irradiating the light, irradiating the visible light, and capturing an image using the imaging device are executed while being shielded from external light.

12. The examination method according to claim 8, further comprising comparing the image of the attached matter with a plurality of reference attached matter images stored in a reference image database.

13. The examination method according to claim 12, further comprising:

controlling the irradiation area, wherein:

in controlling the irradiation area, the object to be examined is irradiated discretely with the light having the specific wavelength as a principal component so as to generate a first attached matter image, an area to be analyzed is identified based on the first attached matter image, and control is implemented to irradiate the area to be analyzed with light so as to generate a second attached matter image; and in comparing, the second attached matter image and the plurality of reference attached matter images are compared.

14. The examination method according to claim 8, further comprising:

measuring a temperature of the object to be examined using a temperature sensor during irradiation of the light having the specific wavelength as a principal component; and controlling the irradiation of the light having the specific wavelength as a principal component, based on the temperature measured by the temperature sensor.

\* \* \* \* \*